(12) United States Patent
Colquitt et al.

(10) Patent No.: US 8,231,541 B2
(45) Date of Patent: Jul. 31, 2012

(54) ASTHMA STATUS SCORING METHOD AND SYSTEM WITH CONFIDENCE RATINGS

(75) Inventors: Nhedti Colquitt, Aloha, OR (US); Deepak Ayyagari, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 842 days.

(21) Appl. No.: 12/288,585

(22) Filed: Oct. 22, 2008

(65) Prior Publication Data

US 2010/0099998 A1    Apr. 22, 2010

(51) Int. Cl.
*A61B 5/08* (2006.01)

(52) U.S. Cl. .............. 600/534; 60/300; 60/537; 60/538; 702/1

(58) Field of Classification Search .......................... None
See application file for complete search history.

(56) References Cited

U.S. PATENT DOCUMENTS

| | | | |
|---|---|---|---|
| 5,632,276 A | 5/1997 | Eidelberg et al. | 600/414 |
| 6,283,923 B1 | 9/2001 | Finkelstein et al. | 600/532 |
| 6,848,144 B1 | 2/2005 | McDonald | 15/246.2 |
| 2001/0055750 A1 | 12/2001 | Rasche et al. | 434/322 |
| 2002/0019747 A1 | 2/2002 | Ware et al. | 705/2 |
| 2005/0115561 A1* | 6/2005 | Stahmann et al. | 128/200.24 |
| 2007/0118054 A1 | 5/2007 | Pinhas et al. | 600/587 |
| 2007/0214013 A1 | 9/2007 | Silverman | 705/2 |
| 2007/0266774 A1 | 11/2007 | Gibson | 73/53.01 |
| 2007/0288266 A1 | 12/2007 | Sysko et al. | 705/2 |
| 2007/0293781 A1 | 12/2007 | Sims et al. | 600/534 |
| 2008/0275349 A1* | 11/2008 | Halperin et al. | 600/484 |
| 2010/0081957 A1* | 4/2010 | Hyde et al. | 600/532 |

FOREIGN PATENT DOCUMENTS

| | | |
|---|---|---|
| GB | 2425180 | 10/2006 |
| JP | 2008-046740 | 2/2008 |
| WO | WO 9963901 | 12/1999 |

OTHER PUBLICATIONS

Schatz et al., Relationships among quality of life, severity, and control measures in asthma: an evaluation using factor analysis, 2005, J Allergy Clin Immunol, 115(5): pp. 1049-1055.*
Zhang et al., "An Endpoint for Worsening Asthma: Development of a Sensitive Measure and its Properties," Drug Information Journal, vol. 38, pp. 5-13 (2004).
Wood et al., "Quantifying Asthma Symptoms in Adults: The Lara Asthma Symptom Scale," Journal of Allergy and Clinical Immunology, vol. 20, pp. 1368-1372 (2007), 1 page abstract.
Quality Metric, Inc., "Asthma Control Test," < http://www.asthmaactionamerica.com/i_have_asthma/control_test_pr.html >, 1 page.
ISA/JP, International Search Report in PCT/JP2009/067317, Dec. 28, 2009, 2 pages.

* cited by examiner

*Primary Examiner* — Nelson C. Yang
(74) *Attorney, Agent, or Firm* — Scot A. Reader

(57) ABSTRACT

A method and system for assessing the health status of a patient, such as the asthma status of a patient, provides an asthma status score and a confidence rating indicative of the score's reliability using continuous real-time data. In some embodiments, the assessment comprises a multidimensional analysis in which asthma status scores and respective confidence ratings are generated for multiple individual asthma health dimensions as well as a summary asthma health dimension indicative of overall asthma health. In some embodiments, the individual dimensions include an environmental trigger dimension based on sensor-based environmental data, a physiological burden dimension based on sensor-based physiological data, a medication adherence dimension based on patient diary data and a perceived symptom dimension based on patient diary data.

14 Claims, 4 Drawing Sheets

ASTHMA STATUS SCORING METHOD AND SYSTEM WITH CONFIDENCE RATINGS

BACKGROUND OF THE INVENTION

The present invention relates to assessing the health status of a patient and, more particularly, to assessing the asthma status of a patient by providing an asthma status score and a confidence rating indicative of the score's reliability using continuous real-time data.

Asthma is an episodic chronic disease that involves disruption of normal respiratory function. One important objective of asthma therapy is preventing episodes of extreme worsening of respiratory function (i.e. asthma attacks) that can lead to hospitalization and even death. To assist in these prevention efforts, the National Institute of Health (NIH) has recommended that asthma sufferers take an Asthma Control Test (ACT) that gives them an idea of how well their asthma has been controlled in the preceding four weeks. The ACT consists of five questions relating to asthma symptoms to which a patient inputs scores that are combined into a total score. A score below 20 (out of a maximum of 25) indicates that the patient's asthma is not well controlled.

Unfortunately, studies have shown that use of the ACT has had only minimal impact in controlling asthma. One problem with the ACT is data reliability. The ACT relies entirely on self-reporting of asthma symptoms. A patient may fail to accurately perceive or assess his or her symptoms, which can cause the patient to delay seeking medical treatment until it is too late. Moreover, the ACT does not take into account the presence or absence of asthma triggers in the patient's environment (e.g. airborne particles, humidity, temperature, etc.). Another problem with the ACT is that the test is taken too infrequently. With more severely affected asthma patients, the ACT is typically performed twice a day. However, the risk of an asthma attack can change in real-time as a patient moves from one environment to another during normal daily activities.

Other asthma scoring approaches have been devised, including computerized approaches that score the asthma status of a patient based at least in part on data collected by sensors mounted on or near the body of a patient. While these approaches rely on reasonable data reliability and increased frequency of testing, they have used a limited set of health attributes and are not known to generate confidence ratings for asthma status scores that indicate the reliability of the scores.

SUMMARY OF THE INVENTION

The present invention, in a basic feature, provides a method and system for assessing the health status of a patient, such as the asthma status of a patient, by providing an asthma status score and a confidence rating indicative of the score's reliability using continuous real-time data. In some embodiments of the invention, the assessment comprises a multidimensional analysis in which asthma status scores and respective confidence ratings are generated for multiple individual asthma health dimensions as well as a summary asthma health dimension indicative of overall asthma health. In some embodiments of the invention, the individual dimensions include an environmental trigger dimension based on sensor-based environmental data, a physiological burden dimension based on sensor-based physiological data, a medication adherence dimension based on patient diary data and a perceived symptom dimension based on patient diary data.

In one aspect of the invention, an assessment system for assessing the asthma status of a patient comprises a data processing system, a data capture system communicatively coupled with the data processing system and an asthma data output system communicatively coupled with the data processing system, wherein the data processing system receives sensor-based data from the data capture system, generates an asthma status score and a confidence rating for the asthma status score based at least in part on sensor-based data and outputs the asthma status score and the confidence rating to the asthma data output system.

In some embodiments, the confidence rating is based at least in part on a comparison of an actual number of parameters used to generate the confidence rating with a maximum number of parameters.

In some embodiments, the confidence rating is based at least in part on a comparison of an actual change rate for the asthma status score with a maximum change rate for the asthma status score.

In some embodiments, the data capture system comprises an environmental data capture system wherefrom the data processing system receives sensor-based environmental data and generates the asthma status score based at least in part on sensor-based environmental data.

In some embodiments, the data capture system comprises a physiological data capture system wherefrom the data processing system receives sensor-based physiological data and generates the asthma status score based at least in part on the sensor-based physiological data.

In some embodiments, the assessment system further comprises a user input system communicatively coupled with the data processing system, wherein the data processing system receives from the user input system patient diary data input by the patient and generates the asthma status score based at least in part on the patient diary data.

In some embodiments, the data processing system generates a plurality of asthma status scores and respective confidence ratings comprising at least one individual asthma status score and individual confidence rating and a summary asthma status score and summary confidence rating.

In some embodiments, the asthma status score is indicative of environmental asthma triggers.

In some embodiments, the asthma status score is indicative of asthma burden on the physiology of the patient.

In some embodiments, the asthma status score is indicative of medication adherence of the patient.

In some embodiments, the asthma status score is indicative of lung function change rate and direction of the patient.

In some embodiments, the environmental data capture system continuously receives environmental sensor data and derives the sensor-based environmental data from the environmental sensor data.

In some embodiments, the physiological data capture system continuously receives physiological sensor data and derives the sensor-based physiological data from the physiological sensor data.

In some embodiments, the data processing system periodically updates the asthma status score and the confidence rating.

In some embodiments, the sensor-based physiological data include at least respiratory data, heart data and saturation of oxygen in arterial blood flow (SpO2) data.

In another aspect of the invention, a method for assessing the asthma status of a patient comprises the steps of receiving sensor-based data, generating an asthma status score and an indicator of reliability of the asthma status score based at least in part on sensor-based data and displaying the asthma status score and the indicator.

In some embodiments, the generating step comprises generating a plurality of asthma status scores and respective indicators of reliability of the asthma status scores comprising at least one individual asthma status score and individual indicator of reliability and a summary asthma status score and summary indicator of reliability.

In some embodiments, the at least one individual asthma status score comprises a plurality of individual asthma status scores including a first score indicative of environmental asthma triggers, a second score indicative of asthma burden on the physiology of the patient, a third score indicative of medication adherence of the patient and a fourth score indicative of symptoms perceived by the patient.

In yet another aspect of the invention, an assessment system for assessing the health status of a patient comprises a data processing system, a data capture system communicatively coupled with the data processing system and a health data output system communicatively coupled with the data processing system, wherein the data processing system receives sensor-based data from the data capture system, generates a health status score and a confidence rating for the health status score based at least in part on sensor-based data and outputs the health status score and the confidence ratings to the health data output system.

In some embodiments, the data processing system generates a plurality of health status scores and respective confidence ratings for the health status scores comprising at least one individual asthma status score and individual confidence rating and a summary asthma status score and summary confidence rating.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
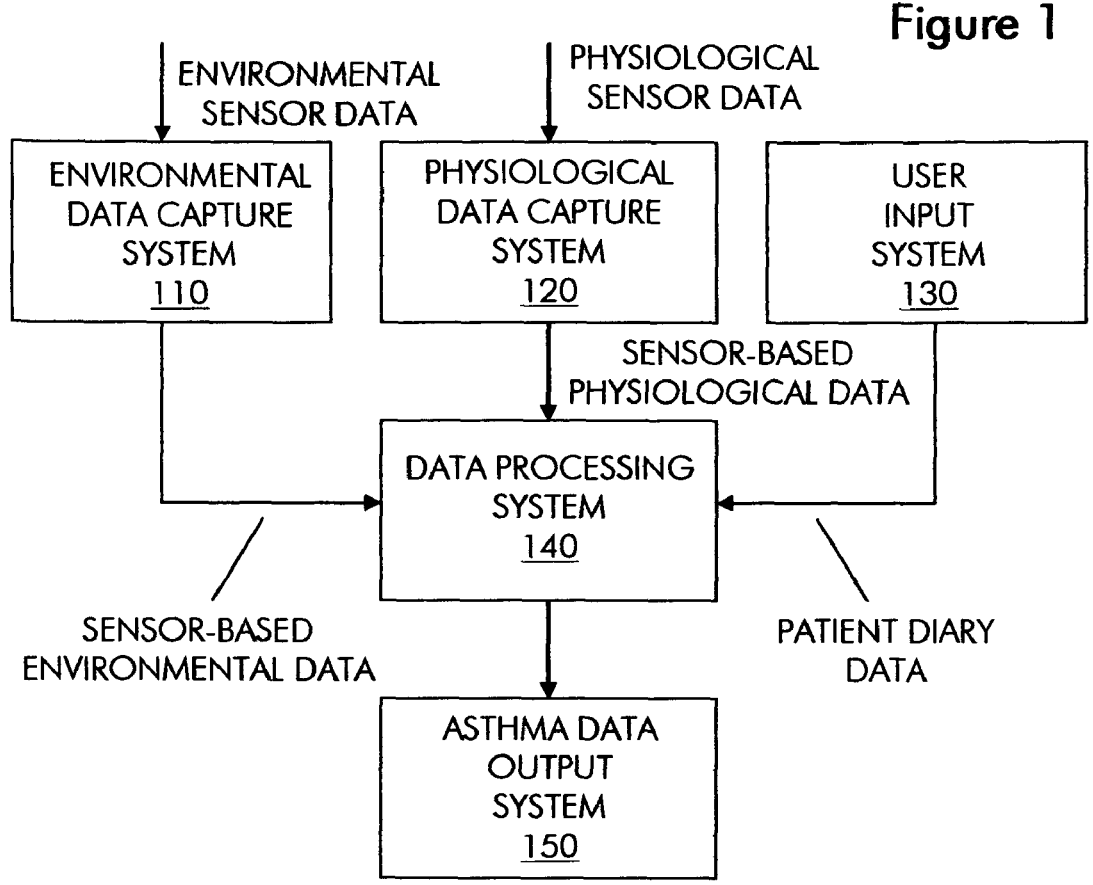
FIG. 1 shows a system for assessing the asthma status of a patient in some embodiments of the invention.

FIG. 1 shows an assessment system for assessing the asthma status of a patient in some embodiments of the invention. The assessment system includes a data processing system 140 communicatively coupled between an environmental data capture system 110, a physiological data capture system 120, a user input system 130 and an asthma data output system 150. Communicative coupling between elements 110, 120, 130, 150, on the one hand, and data processing system 140, on the other, may be realized using wired connections, wireless links, or a combination thereof.

Environmental data capture system 110 continuously receives during operation environmental sensor data. Environmental sensor data are collected by sensors on or near the body of the patient which may include a humidity sensor, a temperature sensor and an airborne particle sensor, for example. Environmental data capture system 110 preprocesses environmental sensor data to generate sensor-based environmental data indicative of environmental asthma triggers. Sensor-based environmental data may include, for example, relative humidity data, ambient temperature data and airborne particulate data, in a form useable by data processing system 140. Environmental data capture system 110 transmits the sensor-based environmental data to data processing system 140. By way of example, preprocessing of environmental sensor data by environmental data capture system 110 may include determining airborne particle density from acquired output voltage measurements indicative of particle density and identification of specific airborne irritants from such output voltage measurements. For instance, if an output voltage pattern consists of several consecutive well above nominal output voltages it may indicate the presence of dense or thick irritants, such as cigarette smoke. If an output voltage pattern, on the other hand, consists of nominal output voltages interrupted by occasional output voltage spikes, it may indicate the presence of thin or less dense irritants, such as scattered pollen or dust.

Physiological data capture system 120 continuously receives during operation physiological sensor data. Physiological sensor data are collected by sensors operative on the body of the patient, which may include a respiratory sound sensor, a heart sound sensor and a pulse oximetry sensor, for example. Physiological data capture system 120 preprocesses the physiological sensor data to generate sensor-based physiological data indicative of the asthma burden on the patient's physiology in a form useable by data processing system 140. Physiological data capture system 120 transmits the sensor-based physiological data to data processing system 140. Preprocessing of physiological sensor data may include, for example, signal amplification, signal filtering, analog to digital (A/D) conversion and time- and/or frequency-domain processing to generate parametric physiological data, such as respiration rate, inspiratory duration, expiratory duration, inspiratory to expiratory ratio (I:E ratio) and SpO2 data.

User input system 130 is an input device, such as one or more of a keyboard, keypad, touch screen, mouse or voice input module, through which the patient inputs patient diary data indicative of asthma symptoms and medication adherence as perceived by the patient. Patient diary data is input into a patient diary form displayed on an output system, such as asthma data output system 150.

Asthma data output system 150 is an output device, such as one or more of an liquid crystal display (LCD) screen or light emitting diode (LED) display screen, through which the patient views asthma output data, such as asthma status scores and confidence ratings for individual and summary asthma health dimensions, as well as patient diary forms. Asthma status scores and confidence ratings displayed on asthma data output system 150 are received from data processing system 140 and updated periodically during operation in accordance with configured time rules. In some embodiments, asthma data output system 150 may have a file capture device and/or printing device in lieu of or in addition to an output display screen.

Data processing system 140 is a processor having software executable thereon for configuring asthma health dimensions, establishing update times for asthma health dimensions, calculating scores and confidence ratings for asthma health dimensions and transmitting scores and confidence ratings for asthma health dimensions to asthma data output system 150 for display thereon. In some embodiments, user input system 130, data processing system 140 and asthma data output system 150 are collocated on a mobile computer, mobile phone, or personal data assistant (PDA).

Figure 2:
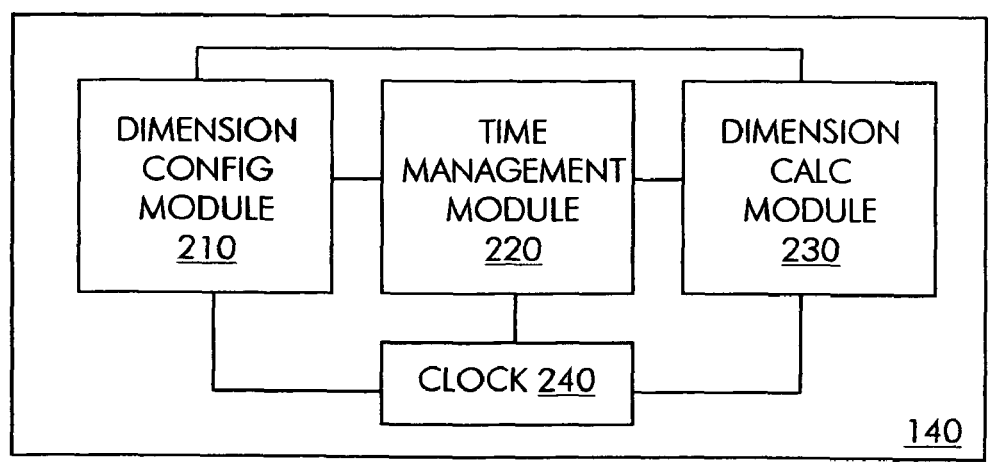
FIG. 2 shows the data processing system of FIG. 1 in more detail.

Data processing system 140 is shown in more detail in FIG. 2 to include a dimension configuration module 210, a time management module 220, a dimension calculation module 230 and a clock 240.

Dimension configuration module 210 is invoked by a programmer to define and register asthma health dimensions. Such a programmer may be a system developer, a system administrator or the patient, for example. Definition and registration of asthma health dimensions takes place in some embodiments at a manufacturer's facility prior to acquisition of the assessment system by the patient, and takes place in other embodiments in the field after acquisition of the assessment system by the patient. Asthma health dimensions are parameter groups indicative of respiratory health that are independently monitored by the assessment system and for which asthma status scores and confidence ratings are independently calculated and outputted. Asthma health dimensions include individual dimensions and, in some embodiments, a summary dimension. Individual dimensions may be selected based on their usefulness as stand-alone predictors of asthma exacerbations. Each individual dimension is defined by the following:

(1) Label—A literal string that uniquely identifies the dimension.
(2) Parameters—Parameters to be included in the scoring calculation.
(3) Score Calculation Rules—Formulas and/or conditional statements used for calculating the asthma status score for the individual dimension using the parameters. These rules include a dimension score algorithm indicating steps for calculating the score. These rules also include a dimension score update frequency that specifies the frequency with which the dimension score should be recalculated and outputted.
(4) Confidence Rating Calculation Rules—Formulas and/or conditional statements for calculating the confidence rating for the individual dimension using the parameters. These rules include one specifying how the fractional number of parameters used to generate the confidence rating (i.e. actual number of parameters used divided by the maximum number of parameters defined for the dimension) impacts on the confidence rating; and one specifying at what point the actual change rate of the score is deemed excessive (i.e. exceeds a maximum change rate) and impacts on the confidence rating. A maximum change rate of "any" may be specified to indicate that the actual change rate of the score, no matter how rapid, does not affect the confidence rating.
(5) Incorporation Rules—Formulas and/or conditional statements for including the asthma status score for the individual dimension in the summary asthma status score calculation. These rules include a summary constraint level. In some embodiments, there are three summary constraint levels: always integrate, integrate only if the confidence rating for the individual dimension exceeds a predetermined threshold, and never integrate.

If a summary dimension is defined, the summary dimension may include the following definitional elements:

(1) Supplemental Score Calculation Rules—Additional formulas and/or conditional statements for calculating the asthma status score for the summary dimension using the asthma status score for the individual dimensions.
(2) Supplemental Confidence Rating Calculation Rules—Additional formulas and/or conditional statements for calculating the confidence rating for the summary dimension using the asthma status score for the individual dimensions.

In some embodiments, five asthma health dimensions are defined, consisting of four individual dimensions and one summary dimension. The individual dimensions include an environmental trigger dimension based on sensor-based environmental data, a physiological burden dimension based on sensor-based physiological data, a medication adherence dimension based on patient diary data and a perceived symptom dimension based on patient diary data. The summary dimension is a composite of the four individual dimensions. In other embodiments, an individual dimension is also defined for lung function change rate and direction based on one or both of sensor-based physiological data or patient diary data.

Figure 3:
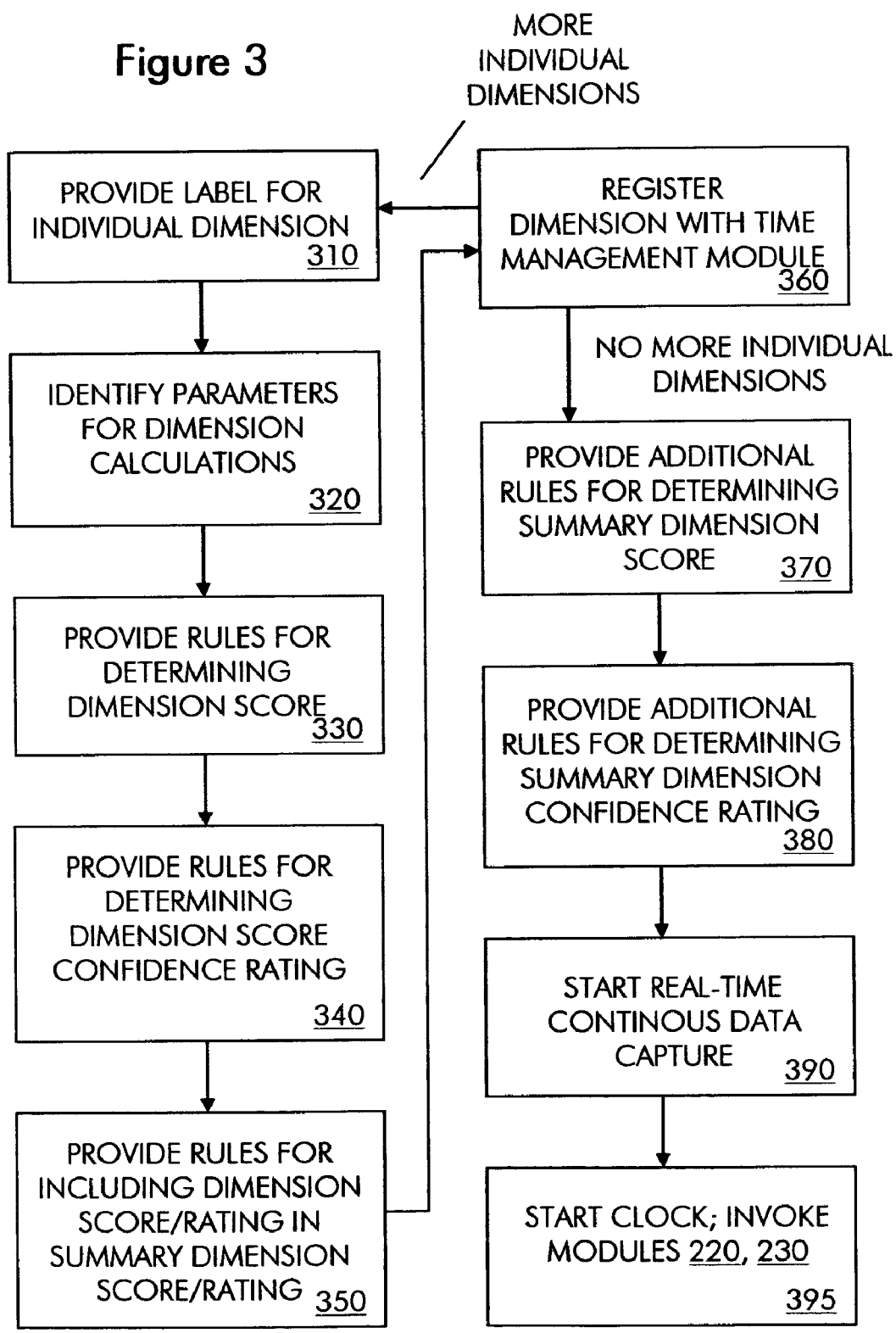
FIG. 3 shows a method for configuring asthma health dimensions in some embodiments of the invention.

FIG. 3 shows a method for configuring asthma health dimensions performed using dimension configuration module 210 in some embodiments of the invention. Configuration may be achieved through programmer interaction with dimension configuration module 210 on user input system 130 or another input system. At the outset, the programmer provides a label for the individual dimension (310). The programmer then identifies parameters to be included in calculations for the individual dimension (320). By way of example, for the environmental trigger dimension, the identified parameters may consist of all sensor-based environmental parameters for which data are received from environmental data capture system 110 (e.g. relative humidity, ambient temperature, and airborne particle identity and concentration).

The programmer then provides rules for determining an asthma status score for the individual dimension (330). For example, in the case of the environmental trigger dimension, the rules may indicate to calculate individual parameter scores between one and five for relative humidity, temperature, and airborne particle concentration and then generate a dimension score between one and five wherein each parameter score contributes one-third to the dimension score. The rules may also indicate a frequency, such as ten minutes, with which the asthma status score for the individual dimension is included in the calculation of the asthma status score for the summary dimension.

The programmer then provides rules for determining a confidence rating indicative of reliability of the asthma status score (340). For example, in the case of the environmental trigger dimension, the rules may indicate to lower the confidence rating if data on fewer than all of relative humidity, ambient temperature and airborne particle concentration are presently available. If, for example, relative humidity data are unavailable at present, the confidence rating may be lowered by one-third from 100% to 67%. The rules may also indicate to lower the confidence rating if a change in the value of any of relative humidity, ambient temperature or airborne particle concentration exceeds a maximum change rate. If, for example, relative humidity data indicate a drop of 3% since the previous reading two seconds ago and the maximum change rate for relative humidity is 1% per second, the confidence rating may be lowered by a predetermined amount.

The programmer then provides rules for including the individual dimension in the summary dimension (350). For example, in the case of the environmental trigger dimension, the rules may indicate to include the individual dimension in the summary dimension calculation only if the confidence rating for the individual dimension exceeds a predetermined threshold, such as 50%. The rules may also indicate an update frequency, such as ten minutes, which is the frequency with which the summary dimension score will be recalculated and transmitted to asthma status output system 150 for display.

Dimension configuration module 210 then registers the individual dimension with time management module 220 (360). Registration includes notifying time management module 220 of the update frequency for the individual dimension.

Once registration of the individual dimension has been completed, the programmer may configure another individual health dimension, such as a physiological burden dimension based on sensor-based physiological data, a medication adherence dimension based on patient diary data or a perceived symptom dimension based on patient diary data. If the programmer elects to configure another individual dimension, Steps 310-360 are repeated. Once there are no more individual health dimensions to configure, the programmer may provide additional rules for determining the asthma status score (370) and the confidence rating (380) for the summary dimension. For example, the rules may indicate an update frequency, such as one minute, which is the frequency with which the asthma status score and confidence rating for the summary dimension will be recalculated and transmitted to asthma status output system 150 for display. Moreover, in some embodiments, additional rules may be established to improve the capability of the asthma status score for the summary dimension to predict the onset of an asthma attack based on current research and prevailing clinical opinion. For example, formulas and/or conditional statements may be configured by which the rate and change of direction of certain respiratory data (e.g. I:E ratio, wheeze rate) are included in the calculation of the asthma status score for the summary dimension.

Once additional rules for the summary dimension have been configured, environmental data capture system 110 and physiological data capture system 120 begin real-time continuous data capture (390), clock 240 is started and time management module 220 and decision calculation module 230 are invoked (395). Naturally, there may be a substantial time lag between configuration and the commencement of real-time continuous data capture depending on who the programmer is and where configuration occurs.

In parallel with the real-time continuous data capture, the patient may submit to data processing system 240 via user input system 130, on an episodic basis, real-time patient diary data for use in calculating asthma status scores and confidence ratings for configured medication adherence and perceived symptom dimensions. Patient diary data may be received when the patient completes or updates a patient diary form rendered on asthma data output system 150. The patient diary form may include questions that allow a patient to describe his or her perceived symptoms, adherence to medication and how asthma has affected his or her daily activities.

Figure 4:
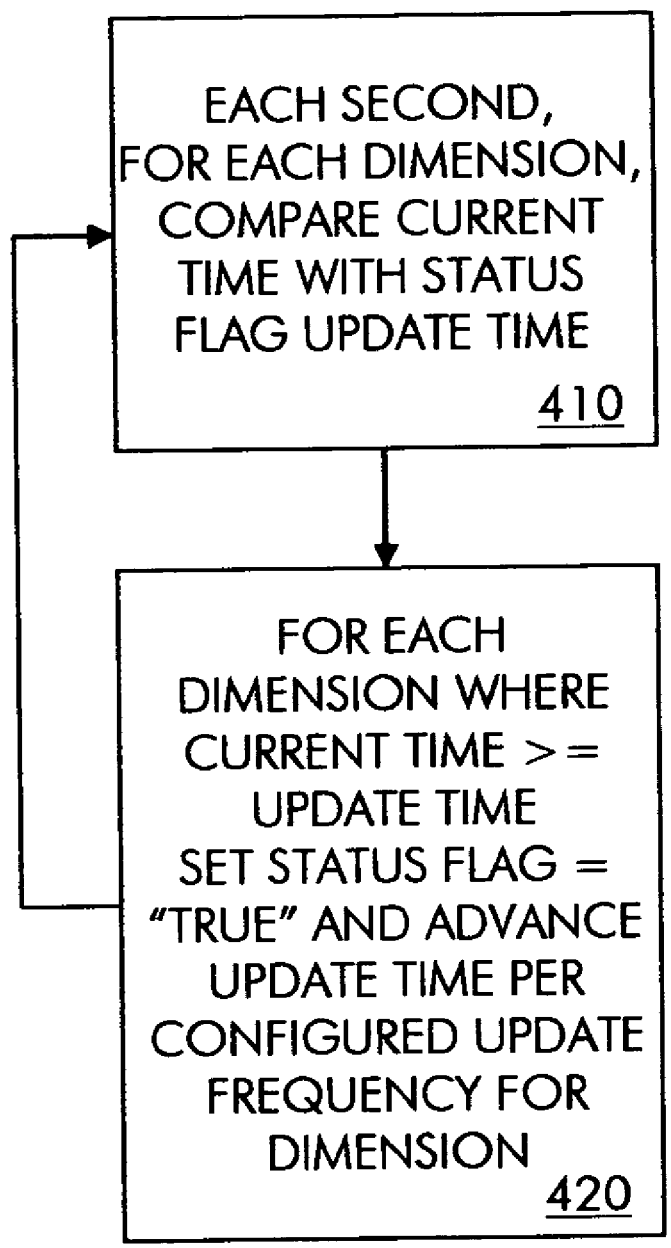
FIG. 4 shows a method for establishing update times for asthma health dimensions in some embodiments of the invention.

FIG. 4 shows a method for establishing update times for asthma health dimensions performed by time management module 220 in some embodiments of the invention. Time management module 220 maintains and manages an update status flag for every configured asthma health dimension. Update status flags are either "TRUE" or "FALSE". Time management module 220 sets an update status flag to "TRUE" at the update frequency for the dimension. Every second, for every dimension, time management module 220 compares the current time kept by clock 240 with a status flag update time (410). For each dimension where the current time is greater than or equal to the update time, module 220 sets the update status flag to "TRUE" and advances the update time in conformance with the configured update frequency for the dimension (420). In this way, dimension calculation module 230 can determine by reference to the update status flags for which dimensions asthma status scores and confidence ratings need to be recalculated and outputted at present.

Figure 5:
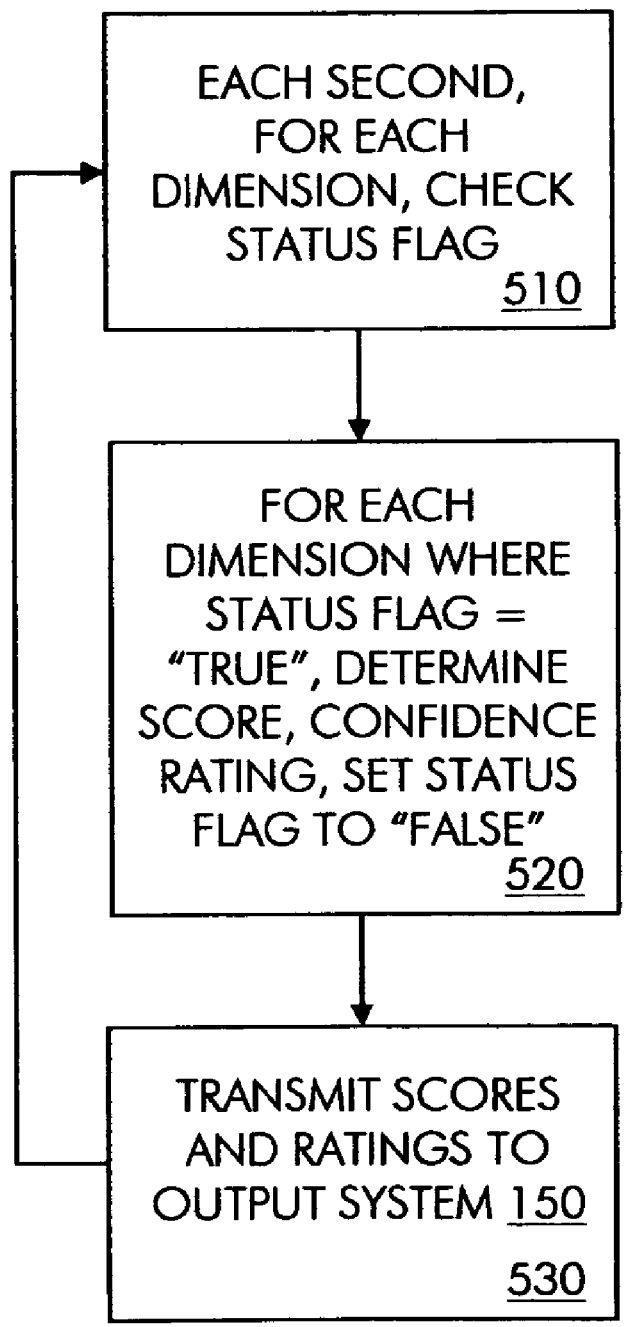
FIG. 5 shows a method for calculating scores and confidence ratings for asthma health dimensions in some embodiments of the invention.

FIG. 5 shows a method for calculating scores and confidence ratings for asthma health dimensions performed by dimension calculation module 230 in some embodiments of the invention. Dimension calculation module 230 determines asthma status scores and confidence ratings for every configured asthma health dimension. Every second, for every dimension, dimension calculation module 230 checks the update status flag (510). For each dimension where the update status flag is "TRUE", module 230 recalculates the asthma status score and confidence rating, and sets the update status flag to "FALSE" (520). Module 230 then transmits the updated asthma status scores and confidence ratings to asthma data output system 150 for display (530).

It will be appreciated by those of ordinary skill in the art that the invention can be embodied in other specific forms without departing from the spirit or essential character hereof. For example, because of the ability of a programmer to configure health dimensions and define parameters and rules, the present method and system can be equally applied to the assessment through scoring and confidence ratings of the status of a patient with respect to other health conditions, such as diabetes and metabolic syndrome. The present description is therefore considered in all respects to be illustrative and not restrictive. The scope of the invention is indicated by the appended claims, and all changes that come within the meaning and range of equivalents thereof are intended to be embraced therein.

What is claimed is:

1. An assessment system for assessing the asthma status of a patient, comprising:
   a data processing system;
   an environmental data capture system communicatively coupled with the data processing system, wherein the environmental data capture system is configured to capture environmental sensor data and generate sensor-based environmental data in a form usable by the data processing system based at least in part on the environmental sensor data; and
   an asthma data output system communicatively coupled with the data processing system, wherein the data processing system is configured to receive the sensor-based environmental data from the environmental data capture system, generate an asthma status score and a confidence rating for the asthma status score based at least in part on sensor-based environmental data and output the asthma status score and the confidence rating to the asthma data output system, wherein the confidence rating is generated based on at least one of a comparison of an actual number of parameters used to generate the asthma status score with a predefined number of parameters or a comparison of an actual change rate for the asthma status score with a predefined change rate, and wherein the asthma data output system is configured to display the asthma status score and the confidence rating.

2. The assessment system of claim 1, wherein the confidence rating is generated based on a comparison of an actual number of parameters used to generate the asthma status score with a predefined number of parameters and a comparison of an actual change rate for the asthma status score with a predefined change rate.

3. The assessment system of claim 1, wherein the data capture system further comprises a physiological data capture system wherefrom the data processing system is configured to receive sensor-based physiological data and is configured to generate the asthma status score further based at least in part on the sensor-based physiological data.

4. The assessment system of claim 1, further comprising a user input system communicatively coupled with the data processing system, wherein the data processing system is configured to receive from the user input system patient diary data input by the patient and is configured to generate the asthma status score further based at least in part on the patient diary data.

5. The assessment system of claim 1, wherein the data processing system is configured to generate a plurality of asthma status scores and respective confidence ratings comprising at least one individual asthma status score and individual confidence rating and a summary asthma status score and summary confidence rating.

6. The assessment system of claim 1, wherein the environmental data capture system is configured to continuously capture the environmental sensor data and continuously derive the sensor-based environmental data from the environmental sensor data.

7. The assessment system of claim 3, wherein the physiological data capture system is configured to continuously capture physiological sensor data and continuously derive the sensor-based physiological data from the physiological sensor data.

8. The assessment system of claim 1, wherein the data processing system is configured to periodically update the asthma status score and the confidence rating.

9. The assessment system of claim 3, wherein the sensor-based physiological data include at least respiratory data, heart data and saturation of oxygen in arterial blood flow (SpO2) data.

10. An assessment system for assessing the health status of a patient, comprising:

a data processing system;
an environmental data capture system communicatively coupled with the data processing system, wherein the environmental data capture system is configured to capture environmental sensor data and generate sensor-based environmental data in a form usable by the data processing system based at least in part on the environmental sensor data; and
a health data output system communicatively coupled with the data processing system, wherein the data processing system is configured to receive sensor-based environmental data from the data capture system, generate a health status score and a confidence rating for the health status score based at least in part on sensor-based environmental data and output the health status score and the confidence rating to the health data output system, wherein the confidence rating is generated based on at least one of a comparison of an actual number of parameters used to generate the health status score with a predefined number of parameters or a comparison of an actual change rate for the health status score with a predefined change rate, and wherein the health data output system is configured to display the health status score and the confidence rating.

11. The assessment system of claim 10, wherein the data processing system is configured to generate a plurality of health status scores and respective confidence ratings for the health status scores comprising at least one individual asthma status score and individual confidence rating and a summary asthma status score and summary confidence rating.

12. The assessment system of claim 1, wherein the sensor-based environmental data comprise relative humidity data.

13. The assessment system of claim 1, wherein the sensor-based environmental data comprise airborne particulate data.

14. The assessment system of claim 10, wherein the confidence rating is generated based on a comparison of an actual number of parameters used to generate the health status score with a predefined number of parameters and a comparison of an actual change rate for the health status score with a predefined change rate.

* * * * *